US010427060B2

(12) United States Patent
Corwin

(10) Patent No.: US 10,427,060 B2
(45) Date of Patent: Oct. 1, 2019

(54) METHODS AND APPARATUS FOR DECORATIVE ATTACHMENT SYSTEM FOR A MEDICAL DEVICE

(71) Applicant: GDI Day Three, LLC, Chandler, AZ (US)

(72) Inventor: Chase Corwin, Chandler, AZ (US)

(73) Assignee: GDI Day Three, LLC, Chandler, AZ (US)

( * ) Notice: Subject to any disclaimer, the term of this patent is extended or adjusted under 35 U.S.C. 154(b) by 23 days.

(21) Appl. No.: 15/659,846

(22) Filed: Jul. 26, 2017

(65) Prior Publication Data

US 2019/0030444 A1 Jan. 31, 2019

(51) Int. Cl.
*A63H 3/00* (2006.01)
*A61M 5/31* (2006.01)
*F16B 2/22* (2006.01)

(52) U.S. Cl.
CPC ............... *A63H 3/003* (2013.01); *A61M 5/31* (2013.01); *F16B 2/22* (2013.01); *A61M 2205/59* (2013.01)

(58) Field of Classification Search
None
See application file for complete search history.

(56) References Cited

U.S. PATENT DOCUMENTS

| 2,166,916 | A | * | 7/1939 | Lombard | F16L 3/13 248/222.12 |
| 2,267,586 | A | * | 12/1941 | Del Camp | F16B 5/125 24/458 |
| 2,469,451 | A | * | 5/1949 | Burrus | F16L 3/13 24/339 |
| 2,539,035 | A | * | 1/1951 | Scanlon | A47K 1/09 194/251 |
| 2,541,828 | A | * | 2/1951 | Peck | H05K 7/12 165/80.3 |
| 2,689,992 | A | * | 9/1954 | Flora | F16B 5/0685 24/293 |
| 2,868,489 | A | * | 1/1959 | Calcut | F16B 5/0685 24/304 |
| 3,154,281 | A | * | 10/1964 | Charles | F16B 21/06 174/138 G |
| 3,212,146 | A | * | 10/1965 | Morgan | B43K 23/001 24/10 R |
| 3,299,891 | A | * | 1/1967 | Smeton | A61M 5/3129 222/78 |
| 3,313,009 | A | * | 4/1967 | Beckerer | F16L 3/13 248/74.2 |
| 3,521,332 | A | * | 7/1970 | Kramer | F16B 2/22 248/229.26 |
| 3,836,703 | A | * | 9/1974 | Coules | H05K 7/142 174/138 D |
| 3,867,742 | A | * | 2/1975 | Austin | F16B 5/0685 24/336 |
| 3,972,628 | A | * | 8/1976 | Stevers | B43L 15/00 15/443 |

(Continued)

*Primary Examiner* — John E Simms, Jr.
*Assistant Examiner* — Urszula M Cegielnik
(74) *Attorney, Agent, or Firm* — The Noblitt Group, PLLC

(57) ABSTRACT

Methods and apparatus for a decorative attachment system for a syringe according to various aspects of the present technology include a figurine and a clip used to connect the figurine to a syringe during use. The clip is configured to be securely attached to the figurine on one end and receive and hold the syringe on a second end.

15 Claims, 4 Drawing Sheets

(56) References Cited

U.S. PATENT DOCUMENTS

| | | | | |
|---|---|---|---|---|
| 4,119,285 A * | 10/1978 | Bisping | ............ | F16L 3/24 248/72 |
| 4,589,794 A * | 5/1986 | Sugiura | ............ | F16B 5/0614 174/138 G |
| 4,973,106 A * | 11/1990 | Strovinskas | ............ | B60R 22/00 280/801.1 |
| 4,976,646 A * | 12/1990 | Hull | ............ | A61J 7/0023 222/78 |
| 5,037,224 A * | 8/1991 | Wright | ............ | B43K 23/04 15/437 |
| 5,038,755 A * | 8/1991 | Burgio | ............ | A61B 1/227 446/72 |
| 5,261,847 A * | 11/1993 | Cox | ............ | A63H 3/44 15/176.4 |
| 5,292,013 A * | 3/1994 | Earl | ............ | H02G 3/263 248/224.61 |
| D347,890 S | 6/1994 | Eads | | |
| 5,590,436 A * | 1/1997 | Wright | ............ | A46B 5/00 15/105 |
| 5,702,371 A * | 12/1997 | Bierman | ............ | A61M 25/02 128/DIG. 26 |
| 5,820,095 A * | 10/1998 | Stone | ............ | B43K 23/00 248/316.7 |
| 5,823,483 A * | 10/1998 | Gaskill | ............ | A47J 43/287 248/37.6 |
| 5,979,843 A * | 11/1999 | Beck | ............ | A61J 9/0669 248/102 |
| 6,015,328 A * | 1/2000 | Glaser | ............ | A46B 5/02 15/167.1 |
| 6,071,131 A * | 6/2000 | Pliml, Jr. | ............ | H01R 4/64 439/95 |
| 6,165,035 A * | 12/2000 | Avner | ............ | A61B 1/227 446/369 |
| 6,299,501 B1 * | 10/2001 | Lynch | ............ | A61J 17/007 446/227 |
| 6,325,695 B1 * | 12/2001 | Weiner | ............ | A61F 7/007 446/295 |
| 6,408,492 B1 * | 6/2002 | Sparks | ............ | A01K 97/08 24/10 R |
| 6,520,639 B2 | 2/2003 | Avner | | |
| 7,055,783 B2 * | 6/2006 | Rosemann | ............ | B60R 16/0215 24/297 |
| 7,219,931 B2 * | 5/2007 | Kato | ............ | B60R 16/0207 248/60 |
| 7,607,627 B1 * | 10/2009 | Mchatet | ............ | B60R 7/082 24/3.12 |
| 8,608,705 B2 * | 12/2013 | Peters | ............ | A61M 25/02 604/174 |
| 8,662,455 B2 * | 3/2014 | Hernandez | ............ | F16B 2/245 248/222.12 |
| D745,144 S | 12/2015 | Aylmer | | |
| 9,427,674 B2 * | 8/2016 | Oi | ............ | F16B 2/22 |
| 9,789,417 B2 * | 10/2017 | Vandoren | ............ | A63H 33/046 |
| 2002/0026152 A1 * | 2/2002 | Bierman | ............ | A61M 25/02 604/174 |
| 2002/0028627 A1 * | 3/2002 | Weiner | ............ | A61F 7/007 446/369 |
| 2002/0082564 A1 | 6/2002 | Pham | | |
| 2004/0245285 A1 * | 12/2004 | McLaughlin | ............ | A61M 5/178 222/78 |
| 2005/0038453 A1 * | 2/2005 | Raulerson | ............ | A61M 25/02 606/151 |
| 2006/0089077 A1 * | 4/2006 | Wittschen | ............ | A61J 7/0053 446/77 |
| 2006/0160458 A1 * | 7/2006 | Peach | ............ | A63H 3/02 446/72 |
| 2007/0281272 A1 | 12/2007 | Rahbari | | |
| 2007/0289770 A1 * | 12/2007 | Koike | ............ | F16B 5/0621 174/153 G |
| 2008/0096459 A1 * | 4/2008 | Mingle | ............ | A61J 1/1462 446/74 |
| 2008/0139076 A1 | 6/2008 | Frasier-Scott | | |
| 2008/0258523 A1 * | 10/2008 | Santin | ............ | B60N 2/5825 297/218.2 |
| 2008/0302932 A1 * | 12/2008 | Mosler | ............ | A61B 5/15003 248/213.2 |
| 2010/0243834 A1 | 9/2010 | Salser | | |
| 2011/0210215 A1 * | 9/2011 | Nitsche | ............ | A61B 5/04085 248/74.1 |
| 2011/0275026 A1 | 11/2011 | Smith | | |
| 2012/0136314 A1 * | 5/2012 | Ciccone | ............ | A61M 25/02 604/174 |
| 2012/0276803 A1 * | 11/2012 | Hernandez | ............ | A45F 3/04 446/75 |
| 2014/0170931 A1 * | 6/2014 | Laurienzo | ............ | A63H 3/003 446/268 |
| 2016/0199264 A1 * | 7/2016 | McClintock | ............ | A63J 17/00 446/73 |
| 2016/0360908 A1 * | 12/2016 | Naraine | ............ | A61J 7/0053 |
| 2017/0043130 A1 * | 2/2017 | Jones | ............ | A61M 25/02 |

* cited by examiner

METHODS AND APPARATUS FOR DECORATIVE ATTACHMENT SYSTEM FOR A MEDICAL DEVICE

BACKGROUND OF THE TECHNOLOGY

The administration of an injection to a person often creates feelings of fear or anxiety within that person. These feelings may be amplified when the injection is being given to a child or toddler. Often, it is the sight of the needle and syringe that trigger the anxious feelings. Similarly, other types of medical equipment such as an otoscope may result in similar feelings by a patient. Various efforts to reduce or lessen these feelings have been attempted and include attempts such as: creating distractions, camouflaging the needle/syringe, numbing the injection site, calm and/or soothing words, and the promise of a reward/prize after the injection is given. These methods have met with varying degrees of success.

SUMMARY OF THE TECHNOLOGY

Methods and apparatus for a decorative attachment system for a syringe according to various aspects of the present technology include a figurine and a clip used to connect the figurine to a syringe during use. The clip is configured to securely attach to the figurine on one end and to receive and hold the syringe on a second end.

BRIEF DESCRIPTION OF THE DRAWINGS

A more complete understanding of the present technology may be derived by referring to the detailed description and claims when considered in connection with the following illustrative figures. In the following figures, like reference numbers refer to similar elements and steps throughout the figures.

Figure 1A:
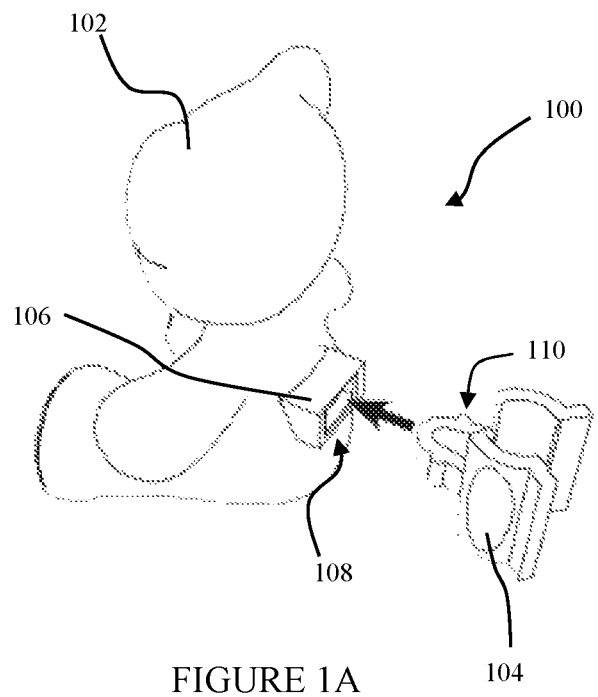
FIG. 1A representatively illustrates a figurine and a detached clip in accordance with an exemplary embodiment of the present technology.
Figure 1B:
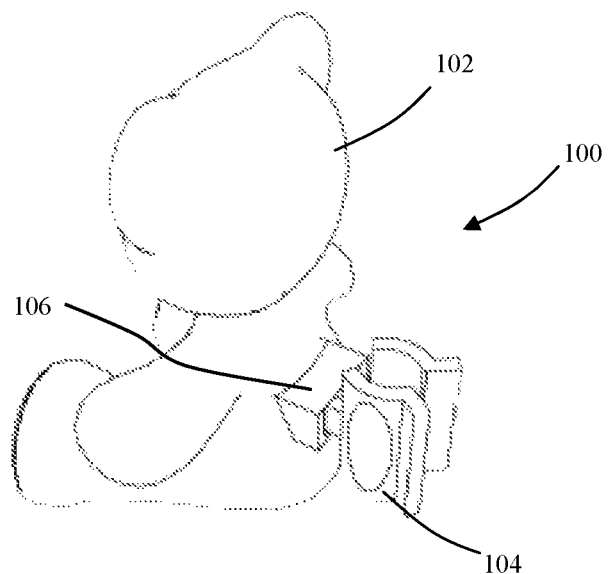
FIG. 1B representatively illustrates the figurine coupled to the clip in accordance with an exemplary embodiment of the present technology.
Figure 2:
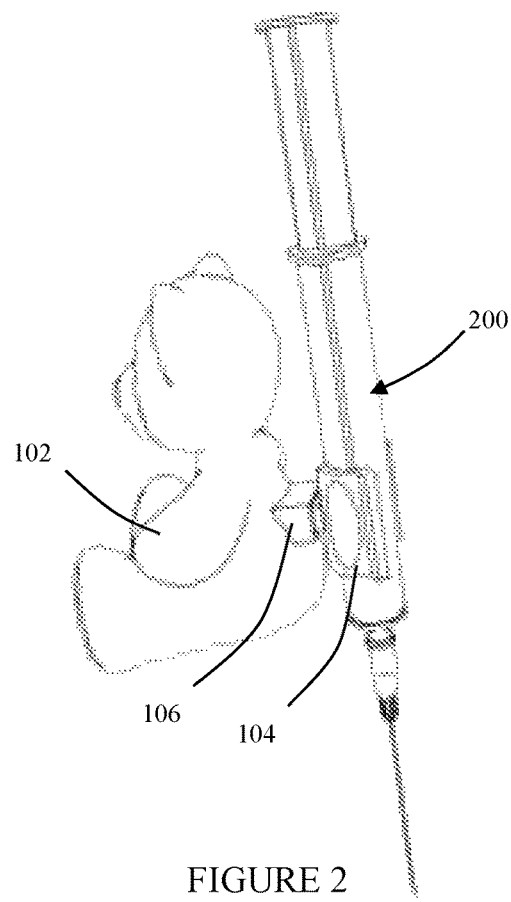
FIG. 2 representatively illustrates a syringe coupled to the clip in accordance with an exemplary embodiment of the present technology.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of hardware components configured to perform the specified functions and achieve the various results. For example, the present technology may employ various materials, syringes, injectables, fasteners, and the like, which may carry out a variety functions. In addition, the present technology may be practiced in conjunction with any number of applications, and the system described is merely one exemplary application for the technology. Methods and apparatus for an attachment device for a syringe according to various aspects of the present technology may operate in conjunction with any suitable medical devices, for example, syringes, aspirators, injectable devices, and/or other similar devices that may cause fear, anxiety, or pain during use.

Referring now to FIGS. 1A, 1B, 2, and 5, a decorative attachment device 100 according to various aspects of the present technology may comprise a figurine 102 and a clip 104 coupled to the figurine 102. The clip 104 may be configured to selectively couple to and hold a syringe 200 during use. The figurine 102 may comprise any suitable toy or statue-like device such as a posable or non-posable figure depicting a human, an animal, a vehicle, or the like. For example, in one embodiment, the figurine 102 may take the form of a teddy bear that can be detached and given to the patient as a reward after the injection is completed.

The figurine 102 may comprise any suitable dimensions that may vary according to the specific type of device or syringe 200 the decorative attachment device 100 is being used with. In general, the figurine 102 may be between about two inches to about five inches in height to at least partially cover the syringe 200 and/or needle to act as a distraction to the patient.

The figurine 102 may comprise any suitable material such as: plastic, rubber, metal, or fabric. The material may be selected according to any suitable criteria such as the ability to be sterilized to allow for use in a hospital or medical examination room. Alternatively, the material may comprise a plush-filled fabric having anti-microbial properties. For example, in one embodiment, the figurine 102 may comprise a molded polymer formed as a single piece with no movable portions or sections that may be removed or otherwise dislodged.

The figurine 102 may comprise a receiving port 106 suitably configured to be coupled to the clip 104. The receiving port 106 may comprise any suitable system or device for connecting the figurine 102 and the clip 104 together such as a coupling, mechanical fastener, frictional fastener, adhesive, or the like. The receiving port 106 may comprise any suitable size or shape to accommodate the clip 104. The receiving port 106 may be positioned at any suitable location on the figurine 102 and may be selected according to any criteria. For example, if the figurine 102 is in the form of an animal or human, the receiving port 106 may be positioned along a rearward facing surface of the figurine 102 so that the front facing portion of the figurine 102 is clearly visible to the patient. The receiving port 106 may also be positioned on the figurine 102 to provide a maximum amount of coverage to the syringe and/or needle so that the patient cannot fully see the syringe and/or needle.

Figure 3:
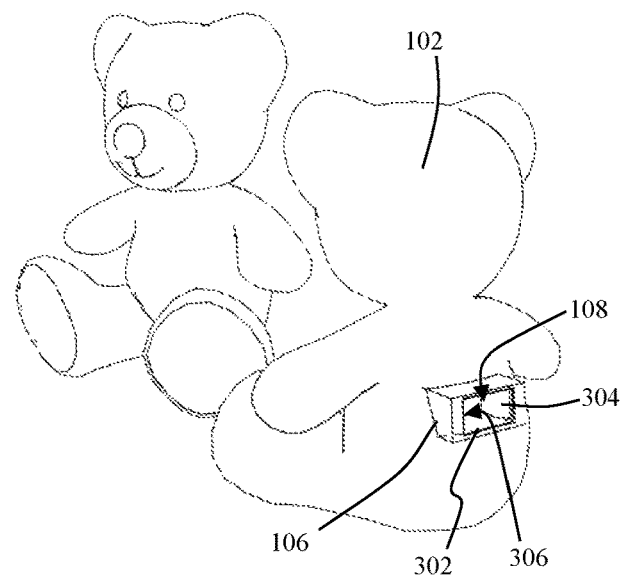
FIG. 3 representatively illustrates a front and rear perspective view of the figurine in accordance with an exemplary embodiment of the present technology.
Figure 4:
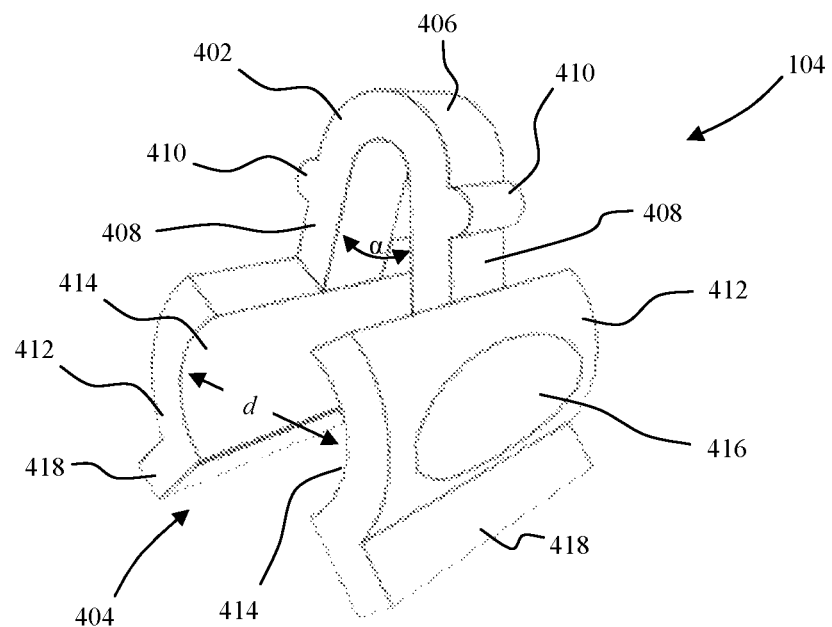
FIG. 4 representatively illustrates a detailed view of the clip in accordance with an exemplary embodiment of the present technology.

Referring now to FIGS. 1A and 3, in one embodiment, the receiving port 106 may comprise a recessed receptacle forming an internal volume 108 configured to receive at least a portion of the clip 104. The recessed receptacle may comprise a substantially rectangular-shaped opening with sidewalls 304, 306 that extend into the figurine 102. The sidewalls may be straight, generally cuboid-shape, or angled to create an increasing or decreasing cross-sectional area of the internal volume 108 along a depth of the recessed receptacle.

The receiving port 106 may be suitably configured to secure, lock, or otherwise temporarily hold the clip 104 in place during use. For example, in one embodiment, the receiving port 106 may comprise a raised lip 302 or ridge positioned along an inner surface near an entrance to the internal volume 108 that is configured to help secure the clip 104 in the receiving port 106 during use. In another embodiment, the receiving port 106 may comprise a spring-loaded locking mechanism that is activated by a button or lever. In yet another embodiment, one or more sidewalls 304, 306 of the internal volume 108 may comprise a recessed section configured to receive a protrusion on the clip 104 to help lock the clip 104 in position.

The clip 104 couples the figurine 102 to the syringe 200 during use. The clip 104 may comprise any suitable device or system to selectively connect, couple, or otherwise temporarily affix the syringe 200 to the figurine 102. The clip 104 may be configured for one-time use or repeated use. For example, the clip 104 may comprise a material such as medical-grade plastics or metals that can be sterilized after use or are hypoallergenic. Alternatively, the clip 104 may comprise a less costly material such as a polymer that can be discarded after use.

Referring now to FIGS. 1A, 1B, 2, and 4, the clip 104 may comprise two main portions: an insertable section 402 configured to be coupled or otherwise secured to the receiving port 106; and a holding portion 404 configured to receive and hold the syringe 200. The insertable section 402 may comprise any suitable device for interacting with the receiving port 106. The insertable section 402 may also comprise a size and shape determined, at least in part, by the size and shape of the internal volume 108 of the recessed receptacle.

In one embodiment, the insertable section 402 may comprise a close ended body having an end portion 406 and two legs 408 depending therefrom. The end portion 406 may comprise any suitable shape such as a generally U-shaped or box-ended structure. The end portion 406 may be rigid or semi-rigid and allow for some level of spring-like tension between the two legs 408. For example, the end portion 406 may comprise a material such as a molded polymer wherein the two legs 408 can be compressed towards each other slightly thereby reducing a distance between the two legs 408. This may allow the overall shape of the clip 104 to be altered temporarily so that the end portion 406 may be positioned inside of the receiving port 106. After the compressive force is removed, the two legs 408 may return to their previous position and press against the sidewalls 304, 306 of the internal volume 108 to hold the clip 104 in position.

The insertable section 402 may further comprise one or more locking elements configured to more securely hold the clip 104 to the figurine 102. The locking elements may comprise any suitable device or feature configured to maintain the connection between the clip 104 and the figurine 102. For example, in one embodiment, the insertable section 402 may comprise a first protrusion 410 extending outwardly from one of the two legs 408 and a second protrusion 410 extending outwardly from the remaining leg. The first and second protrusions 410 may be suitably configured to increase a pressure force against the sidewalls 304, 306. Alternatively, a distance between a tip of the first and second protrusions 410 may be greater than a distance separating opposing edges of the raised lip 302 such that the first and second protrusions 410 are locked within the internal volume 108 of the recessed receptacle. However, when the two legs 408 are compressed, the distance between the tip of the first and second protrusions 410 may be less than the distance between the opposing edges of the raised lip 302 thereby allowing the insertable section 402 to be removed from the receiving port 106.

In an alternative embodiment, the locking element may comprise a single protrusion extending outward from an outer surface of the insertable section 402 that is configured to snap into place against a mating recess or hole in the receiving port 106. For example, the locking element may comprise a raised dome-like surface or button positioned on at least one of the two legs 408. The button may then snap into a mating hole in an interior surface or sidewall 304, 306 of the receiving port 106.

The holding portion 404 is configured to securely hold the syringe adjacent to the figurine 102 during use. The holding portion 404 may comprise any suitable system or device for receiving and holding the syringe or any similar cylindrically-shaped body. With continued reference to FIG. 4, in one embodiment, the holding portion 404 may comprise a pair of receiving sections 412. Each receiving section 412 may be positioned at or near an end portion of one of the two legs 408. For example, a first receiving section 412 may be coupled to an end of a first leg 408 and a second receiving section 412 may be coupled to an end of a second 408.

The pair of receiving sections 412 may be coupled to the two legs 408 by any suitable method. In one embodiment, the pair of receiving sections 412 may be mechanically coupled to the two legs 408 by a fastener such as a screw, bolt, adhesive, or the like. In a second embodiment, the pair of receiving sections 412 may be integrated into the two legs 408 as a unitary structure of molded plastic.

Each receiving section 412 may comprise a surface configured to at least partially conform to the syringe 200. In one embodiment, the first and second receiving sections 412 may comprise a curved surface 414 configured to fit around a portion of an outer surface of a cylindrical body portion of the syringe 200. The curved surface 414 may comprise any suitable size or shape. For example, the curved surface 414 may comprise a concave surface such that the curved surfaces 414 of the first and second receiving section 412 form opposing pressure surfaces for receiving and holding the syringe 200.

A center portion of the curved surfaces 414 may be positioned a pre-determined distance "d" apart due, at least in part, to an angle "α" formed between the two legs 408 and/or a radius of curvature of the curved surfaces 414. The distance d may comprise any suitable amount and may be determined according to any suitable criteria such as the size of the syringe 200 being used. The distance d between the curved surfaces 414 may be configured to be less than a diameter of the syringe to increase a holding force on the syringe applied by the curved surfaces 414. For example, the clip 104 may comprise a single semi-rigid piece of molded plastic and the distance d between the curved surfaces may be about one-eighth of an inch. A syringe 200 having a diameter greater than one-eighth of an inch may be inserted into the space separating the curved surfaces 414. Since the diameter of the syringe 200 is larger than the pre-determined distance d, the two receiving sections 412 are pushed away from each other.

This may create a holding force against the curved surfaces 414 that is opposed by the two legs 408 and the closed end portion 406 of the clip 104. This holding force may be used to securely hold the syringe 200 in position during use. The amount of holding force may be adjusted by any suitable method such as: the rigidity of the material used to make the clip 104, the angle α, the length of the two legs 408, the radius of curvature of the curved surfaces, the size of the syringe 200 or any combination thereof.

The clip 104 may further be configured to receive various sizes of syringes. For example, the clip 104 may comprise a material that allows the first and second receiving sections 412 to be separated by several factors of distance d to allow the clip 104 to securely hold syringes that have diameters of about four to five times greater than distance d.

When the syringe 200 is positioned within the holding portion 404, the clip 104 may be prevented from being removed from or otherwise decoupled from the figurine 102. For example, the presence of the syringe 200 between the pair of receiving sections 412 will prevent the pair of receiving sections 412 from being pressed towards each other. This prevents the first and second protrusions 410 from being compressed together, locking them in place within the internal volume 108 until a user removes the syringe 200.

An outward facing surface of one or more of the receiving sections 412 may comprise an ergonomic feature to improve handling of the decorative attachment device 100 during use. For example, in one embodiment, an outward facing surface of each of the first and second receiving portions 412 may comprise a recessed surface 416 for receiving a user's finger. The recessed surface 416 may comprise a surface treatment to provide additional tactile feel. For example, in one embodiment, the surface treatment may comprise a textured surface configured to reduce slippage. In a second embodiment, the surface treatment may comprise a rubberized coating for increasing a coefficient of friction between a user's finger and the first and second receiving portions 412.

Each receiving section 412 may further comprise a flared end portion 418. The flared end portion 418 may act as a guide to help the user insert the syringe 200 into the space between the first and second receiving portions 412. The flared end portion 418 may also help the user remove the syringe from the clip 104 after use by providing a point of leverage to separate the first and second receiving portions 412.

Figure 5:
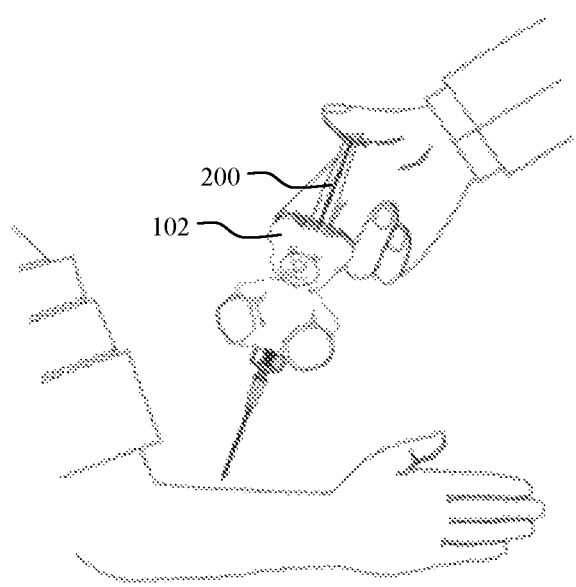
FIG. 5 representatively illustrates the attachment system in use in accordance with an exemplary embodiment of the present technology.
Figure 6:
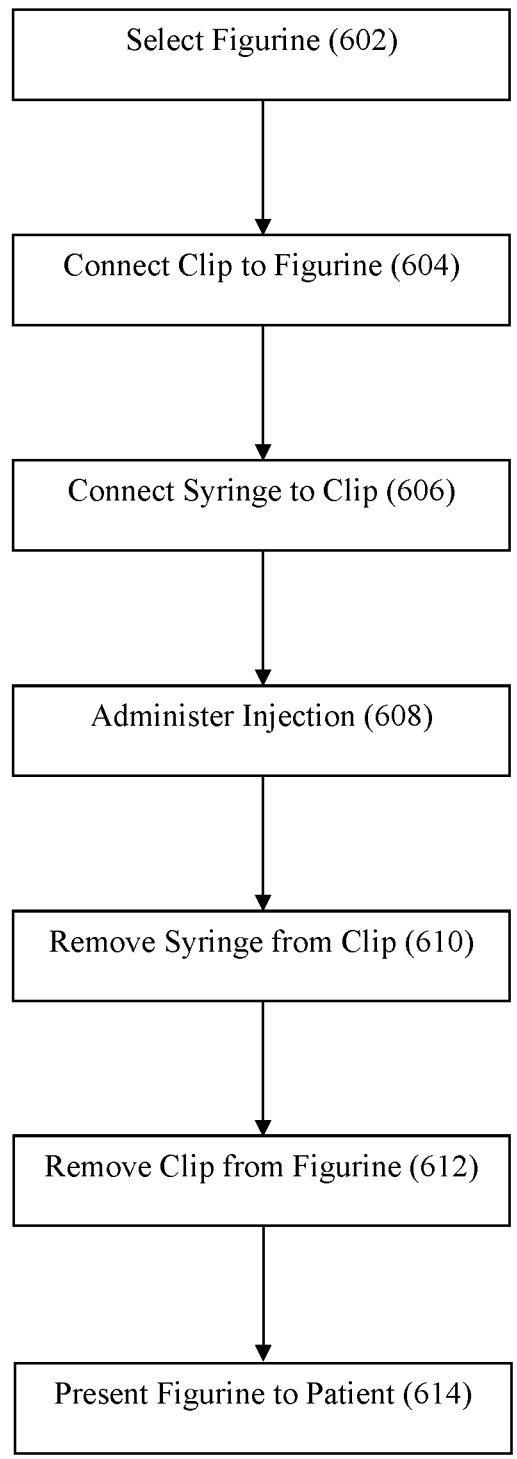
FIG. 6 is a flowchart for use of the attachment system in accordance with an exemplary embodiment of the present technology.

Referring to FIG. 6, in operation, the decorative attachment device 100 is used to help distract or alleviate feelings of anxiety patients may experience when receiving an injection. A medical professional may select a figurine 102 (602) and then position an insertable section 402 of the clip 104 into the figurine (602). Once the figurine 102 and clip 104 are coupled together, the syringe 200 may be positioned within the holding portion 404 of the clip 104 (606). The medical professional may then administer the injection to the patient (as shown in FIG. 5) (608). After the injection has been given, the syringe 200 may be removed from the clip (610) and discarded. The clip 104 may then be removed from the figurine 102 and discarded (612). The figurine 102 may then be given to the patient as a reward (614).

These and other embodiments for methods of forming an attachment system for a syringe may incorporate concepts, embodiments, and configurations as described above. The particular implementations shown and described are illustrative of the technology and its best mode and are not intended to otherwise limit the scope of the present technology in any way. For brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to an exemplary embodiment. However, changes and modifications may be made to the exemplary embodiment without departing from the scope of the present technology. These and other changes or modifications are intended to be included within the scope of the present technology, as expressed in the following claims.

The invention claimed is:

1. An attachment system for a medical device, comprising:
   a figurine having a receiving port recessed into the figurine; and
   a one piece removable clip comprising:
     an insertable section, comprising:
       a curved end portion configured to be secured fully within the receiving port;
       a first leg:
          extending away from a first side of the curved end portion that is disposed within the receiving port when the curved end portion is secured within the receiving port; and projecting outward from the receiving port when the curved end portion is secured within the receiving port;

a second leg:
  extending away from a second side of the curved end portion that is disposed within the receiving port when the curved end portion is secured within the receiving port; and
  projecting outward from the receiving port when the curved end portion is secured within the receiving port, wherein an open space:
    is formed between the first and second legs; and
    is at least partially disposed within the receiving port when the curved end portion is secured within the receiving port; and a locking element disposed along at least one leg and configured to abut at least one internal sidewall of the receiving port to secure the removable clip to the figurine when the curved end portion is secured within the receiving port; and a holding portion immediately adjacent to and extending outwardly from the first and second legs of the insertable section, wherein the holding portion is configured to receive the medical device.

2. An attachment system for a medical device according to claim 1, wherein the locking element comprises:
  a first protrusion extending outwardly from the first leg to engage a first internal sidewall of the receiving port; and
  a second protrusion extending outwardly from the second leg to engage a second internal sidewall of the receiving port opposite the first internal sidewall of the receiving port.

3. An attachment system for a medical device according to claim 2, wherein the receiving port comprises a lip adjacent to an outer edge of the receiving port and is configured to lock the first and second protrusions inside of the receiving port.

4. An attachment system for a medical device according to claim 2, wherein the holding portion comprises:
  a first receiving portion coupled to an end of the first leg and extending outwardly away from the receiving port; and
  a second receiving portion coupled to an end of the second leg and extending outwardly away from the receiving port.

5. An attachment system for a medical device according to claim 4, wherein an inward facing surface of each of the first and second receiving portions comprises a curved surface configured to conform to an exterior surface of the medical device.

6. An attachment system for a medical device according to claim 4, wherein an outward facing surface of each of the first and second receiving portions comprises a recessed surface.

7. A decorative attachment device for a syringe, comprising:
  a figurine having a receiving port;
  a generally U-shaped body configured to be selectively coupled to the receiving port comprising:
    a curved end portion configured to be inserted fully within the receiving port;
    a first leg extending away from a first side of the curved end portion and outward from the receiving port when the curved end portion is inserted within the receiving port;
    a second leg extending away from a second side of the curved end portion and outward from the receiving port when the curved end portion is inserted within the receiving port, wherein an open space:
      is formed between the first and second legs; and
      is at least partially disposed within the receiving port when the U-shaped body is coupled to the receiving port;
    a first protrusion extending outwardly from the first leg to engage a first internal wall of the receiving port; and
    a second protrusion extending outwardly from the second leg to engage a second internal wall of the receiving port, wherein the first and second protrusions are positioned within the receiving port when the U-shaped body is coupled to the receiving port;
    a first receiving portion coupled to an end of the first leg and extending away from the receiving port; and
    a second receiving portion coupled to an end of the second leg and extending away from the receiving port.

8. A decorative attachment device according to claim 7, wherein the receiving port comprises a lip adjacent to an outer edge of the receiving port and configured to lock the first and second protrusions inside of the receiving port.

9. A decorative attachment device according to claim 7, wherein an inward facing surface of each of the first and second receiving portions comprises a concave surface configured to conform to an exterior surface of the syringe.

10. A decorative attachment device according to claim 9, wherein each of the first and second receiving portions comprises a flared end portion extending outwardly away from the concave surface.

11. A decorative attachment device according to claim 7, wherein an outward facing surface of each of the first and second receiving portions comprises a recessed surface.

12. A method of giving an injection, comprising:
  selecting a figurine;
  inserting a one piece removable clip into a receiving port disposed on the figurine, wherein the clip comprises:
    a curved end portion and two legs depending outwardly therefrom;
    a first protrusion extending outwardly from a first leg; and
    a second protrusion extending outwardly from a second leg opposite the first leg, wherein the first and second protrusions are positioned within the receiving port when the clip is coupled to the receiving port;
  coupling a syringe to a holding portion of the clip, wherein the holding portion is immediately adjacent to and extends outwardly from the figurine;
  decoupling the syringe from the holding portion after the injection has been given; and
  removing the clip from the receiving port of the figurine.

13. A method of according to claim 12, wherein inserting the clip into the receiving portion comprises pressing two opposing sides of the holding portion towards each other to compress a pair of locking protrusions extending outwardly from the clip.

14. A method of according to claim 12, wherein the holding portion comprises:
  a first receiving portion coupled to an end of the first leg of the clip; and
  a second receiving portion coupled to an end of the second leg of the clip, wherein an inward facing surface of each of the first and second receiving portions comprises a curved surface configured to conform to an exterior surface of the syringe.

15. A method of according to claim 14, wherein an outward facing surface of each of the first and second receiving portions comprises a recessed surface.

\* \* \* \* \*